US010529031B2

(12) United States Patent
Ganesamoorthi et al.

(10) Patent No.: US 10,529,031 B2
(45) Date of Patent: Jan. 7, 2020

(54) METHOD AND SYSTEMS OF IMPLEMENTING A RANKED HEALTH-CONTENT ARTICLE FEED

(71) Applicants: Sai Suresh Ganesamoorthi, Fremont, CA (US); Aravind Kilaru, Garland, TX (US)

(72) Inventors: Sai Suresh Ganesamoorthi, Fremont, CA (US); Aravind Kilaru, Garland, TX (US)

(*) Notice: Subject to any disclaimer, the term of this patent is extended or adjusted under 35 U.S.C. 154(b) by 1140 days.

(21) Appl. No.: 14/864,859

(22) Filed: Sep. 24, 2015

(65) Prior Publication Data
US 2016/0188601 A1    Jun. 30, 2016

Related U.S. Application Data

(60) Provisional application No. 62/055,071, filed on Sep. 25, 2014.

(51) Int. Cl.
*G06Q 50/00* (2012.01)
*G06F 19/00* (2018.01)

(52) U.S. Cl.
CPC .......... *G06Q 50/01* (2013.01); *G06F 19/324* (2013.01)

(58) Field of Classification Search
CPC .... G06Q 30/0277; G06Q 30/02; G06Q 50/01; G06F 16/3322; G06F 16/951; G06F 19/324
See application file for complete search history.

(56) References Cited

U.S. PATENT DOCUMENTS 8,255,386 B1 * 8/2012 Annau ................ G06F 16/22
707/711
8,880,498 B2 * 11/2014 Rubanovich .......... G06F 16/951
707/709

(Continued)

OTHER PUBLICATIONS

Kiley, Robert. "Quality of Medical Information on the Internet." Journal of the Royal Society of Medicine. vol. 91. Jul. 1998. pp. 369-370 (Year: 1998).*

*Primary Examiner* — Linh Giang Le

(57) ABSTRACT

A computerized method for implementing a ranked health-content article feed includes the step of obtaining a set of health-content articles. A health-content article includes a distributable computer file containing a media content comprising text, a digital image or a digital video. The method includes the step of identifying a sub-set of health content articles comprising a marketing content. The method includes the step of removing the sub-set of health content articles comprising the marketing content from the set of health-content articles. The method includes the step of providing an authority score for each health-content article of the set of health-content articles. The method includes the step of providing a social-popularity score for each health-content article of the set of health-content articles. The method includes the step of providing a content score for each health-content article of the set of health-content articles. The method includes the step of aggregating the authority score, the social popularity score and the content score for each health-content article. The method includes the step of ranking the set of health-content articles based on an aggregated score of each health-content article. The method includes the step of distributing a ranked set of health-content articles to a consumer entity in a web-feed format.

5 Claims, 8 Drawing Sheets

(56) References Cited

U.S. PATENT DOCUMENTS

| | | | | |
|---|---|---|---|---|
| 2013/0031034 A1* | 1/2013 | Gubin | ............ | G06Q 10/06393 706/12 |
| 2013/0346545 A1* | 12/2013 | Petersen | ................ | H04L 67/10 709/217 |
| 2014/0304247 A1* | 10/2014 | Fastlicht | ................ | G06F 16/40 707/706 |

* cited by examiner

METHOD AND SYSTEMS OF IMPLEMENTING A RANKED HEALTH-CONTENT ARTICLE FEED

CROSS-REFERENCE TO RELATED APPLICATIONS

This application is a claims priority from U.S. Provisional Application No. 62/055,071, titled METHOD AND APPARATUS FOR SOURCING RANKED ONLINE PATIENT EDUCATION CONTENT FEEDS and filed 25 Sep. 2014. This application is hereby incorporated by reference in its entirety.

FIELD OF THE INVENTION

The present invention is in the technical field of health information technology. More particularly, the present invention is in the technical field of ranking online patient education content.

DESCRIPTION OF THE RELATED ART

Each day, thousands of patient education articles are published online for various medical conditions such as diabetes, asthma, breast cancer, depression, etc. and health topics such as healthy living, healthy eating, smoking, sleep, etc. Such content is published by various entities such as the editorial staff of large hospitals, news agencies, blog writers, patient education content companies, health agencies, government agencies etc. The gamut of content publisher types that produce patient education content may lead to significant differences in the quality of content published, necessitating the use of automated content ranking engines that scores and ranks online content.

A common content ranking engine that people are used to is a search engine such as Google, Yahoo, etc. These search engines use the same algorithm to rank content immaterial of the field of the content. For example, a search query in the field of sports is handled the same way as a search query the field of health. Typical search queries that people perform may be informational, such as when a user is looking for a specific piece of information. For example, when a user is looking for information to take an action such as buying a product, etc. Accordingly, search engine results may be typically optimized for these use cases.

An alternate use case for a content ranking engine is one where, instead of the user having to type his/her informational search engine query every day, a content feeds can be automatically brought to the user. A common technology that people use for this use case is RSS (Really Simple Syndication). RSS can allows users to keep up with news and information that is important to the user, as well as help the user avoid the conventional methods of browsing or searching for information on websites. The user subscribes to a website's RSS and this removes the need for the user to manually check the website for new content. Instead, the user's browser constantly monitors the site and informs the user of any updates.

A user suffering from a chronic medical condition may want to track of information published online for a specific condition. A typical use case here would be for the user to subscribe to RSS feeds from various websites that feature content for that specific condition. One problem with this approach, however, can arise when the user would have to manually subscribe to the RSS feeds of various websites, one at a time and make changes to this list of websites based on the quality of content seen from a specific website. Also, the user may be inundated with a deluge of content because RSS informs the user anytime a new content is being published. Also, the RSS feeds are not ranked based on the quality of the content.

SUMMARY OF INVENTION

A computerized method for implementing a ranked health-content article feed includes the step of obtaining a set of health-content articles. A health-content article set includes a distributable computer file containing a media content comprising text, a digital image or a digital video. The method includes the step of identifying a sub-set of health content articles comprising a marketing content. The method includes the step of removing the sub-set of health content articles comprising the marketing content from the set of health-content articles. The method includes the step of providing an authority score for each health-content article of the set of health-content articles. The method includes the step of providing a social-popularity score for each health-content article of the set of health-content articles. The method includes the step of providing a content score for each health-content article of the set of health-content articles. The method includes the step of aggregating the authority score, the social popularity score and the content score for each health-content article. The method includes the step of ranking the set of health-content articles based on an aggregated score of each health-content article. The method includes the step of distributing a ranked set of health-content articles to a consumer entity in a web-feed format.

Figure 1:
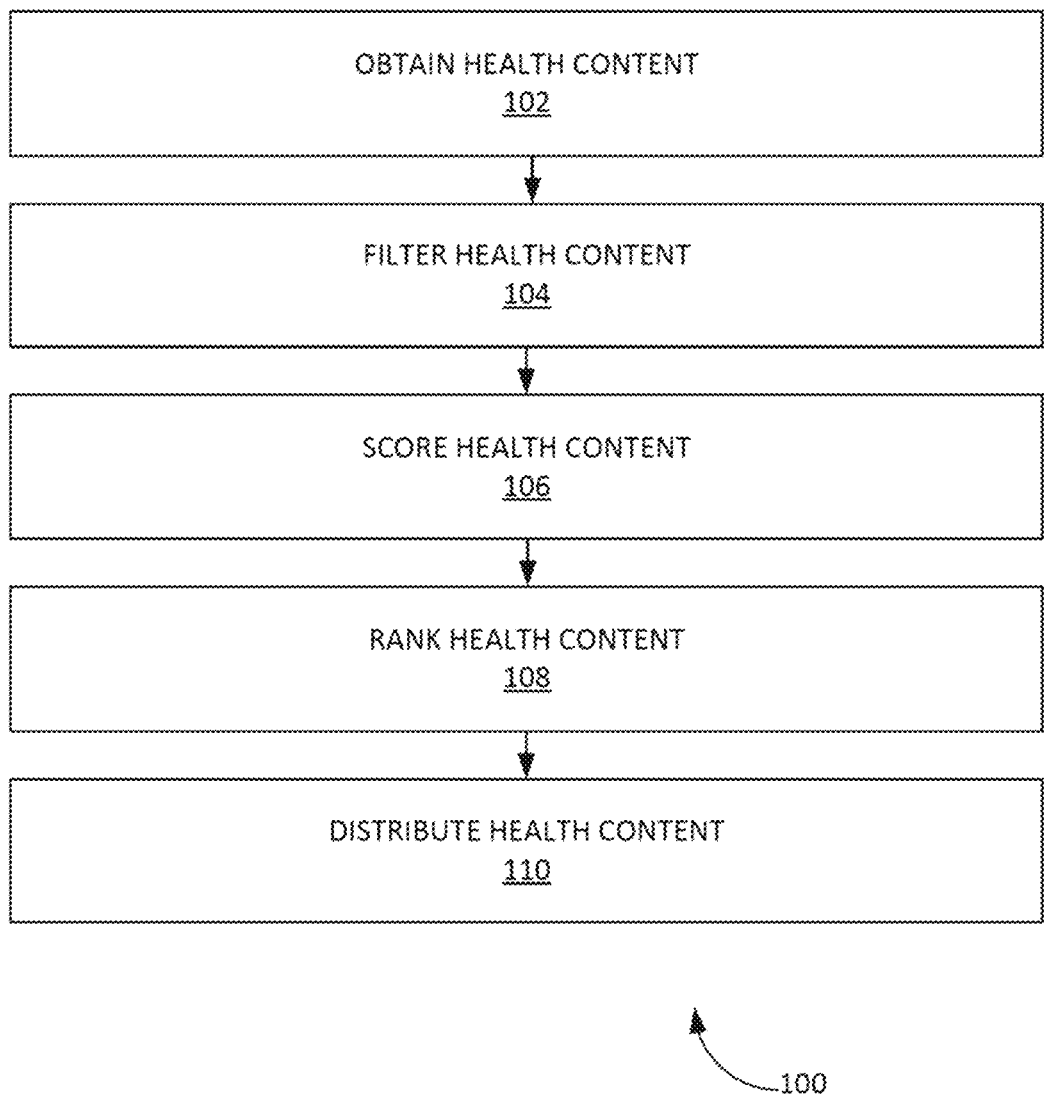
FIG. 1 illustrates an example process for providing ranked health content to a consumer, according to some embodiments.

The Figures described above are a representative set, and are not an exhaustive with respect to embodying the invention.

DESCRIPTION

Disclosed are a system, method, and article of manufacture of a implementing a ranked health-content article feed. The following description is presented to enable a person of ordinary skill in the art to make and use the various embodiments. Descriptions of specific devices, techniques, and applications are provided only as examples. Various modifications to the examples described herein can be readily apparent to those of ordinary skill in the art, and the general principles defined herein may be applied to other examples and applications without departing from the spirit and scope of the various embodiments.

Reference throughout this specification to "one embodiment," "an embodiment," 'one example,' or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art can recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, and they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Exemplary Definitions

Anchor text can include the visible, clickable text in a hyperlink and/or associated text in a microblog (e.g. a tweet on Twitters) or other post (e.g. a Facebook® post, a LinkedIn® post, etc.).

Quantitative text analysis can be a set of techniques that extracts semantic and/or grammatical relationships between words in order to determine the meaning and/or stylistic patterns of, usually, a casual personal text for the purpose of psychological profiling etc.

Ranking can be a relationship between a set of items such that, for any two items, the first is either 'ranked higher than', 'ranked lower than' or 'ranked equal to' the second.

Sentiment analysis can include discerning subjective material and/or extracting various forms of attitudinal information: sentiment, opinion, mood, and emotion.

Text mining can include the process of deriving information from text. Text mining can analyze various patterns and trends in text through means such as statistical pattern learning. Text mining usually can involve the process of structuring the input text (e.g. parsing, along with the addition of some derived linguistic features and the removal of others and subsequent insertion into a database), deriving patterns within the structured data, and/or evaluation and interpretation of the output.

Web crawler can be an Internet bot that systematically browses the World Wide Web (e.g. for the purpose of Web indexing).

A web feed (or news feed) can be a data format used for providing users with updated content. A content distributors can syndicate a web feed, thereby allowing usersiconsumers to subscribe to it.

Exemplary Methods

FIG. 1 illustrates an example process 100 for providing ranked health content to a consumer, according to some embodiments. In some examples, health content can include any content that provides a user information about human health, pet health, various medical service information, etc. Process 100 can provide a consumer high-quality health content from multiple sources in the form of a continuous content stream. A consumer can be a hospital, other healthcare provider, veterinary service, government health entity, non-profit health-related organization, etc. The health content can be ranked and filtered health content that is present in a web-feed format (e.g. RSS or other type of newsfeed). Consumers can provide and entity that implements process 100 various options, preferences and the like such that the health content in the web-feed format is related to a particular health-content topic (e.g. diabetes, heart disease, cancer, infant health, pet health, agricultural livestock health, etc.).

In one example, in step 102, process 100 can obtain health content. For example, process 100 can utilize a web crawler to obtained from a health-content source from social media websites (e.g. Facebook®, Twitters, LinkedIn®, etc.), an online health-news services (e.g. WebMD®, etc.), etc. In other examples, process 100 can obtain the health content via an API from a health-content source. Process 100 can also obtain metadata about the health content. In the event the health content is obtained from a social networking post (e.g. a microblog post, a status update, etc.), process 100 can obtain the anchor text of the post that links to a health-content article (e.g. article, blog post, digital research paper, e-book, podcast, digital video, etc.).

In one example, process 100 can search for health content that is popular on one or more social media websites. Process 100 can follow the link and obtain the content of the linked article, the anchor text, statistics about the post (e.g. number of views, 'likes', retweets, favourites, etc.).

In step 104, process 100 can filter the health content. For example, process 100 can utilize various analytics to determine that the content is marketing content. Process 100 can remove marketing content. Process 100 can include a list of black-listed content sources. Process 100 can remove content from black-listed content sources. These filtering methods are provided by way of example and not of limitation. Other filtering methods can also be applied (e.g. see infra).

In step 106, process 100 can score the remaining health content. A health content can be scored based on several parameters (e.g. authority of health-content source, popularity of health-content source, curating, etc.). An example of step 106 if provided infra. In step 108, process 100 can rank the scored-health content based on the score determined in step 106.

In step 110, process 100 can distribute the health content. For example, the health content can be sorted based on rank and other factors (e.g. topic, consumer options, etc.). The health content can be formatted to be digitally distributed on a hospital and/or medical company portal (e.g. a site that functions as a point of access to information for the hospital and/or medical company on a computer network). Portals from hospitals and medical companies. In this way, a user (e.g. a patient) can view the top ranked health content via the Internet (e.g. as a widget on a web page on a hospital patient portal). The content can be changed/updated on a periodic basis.

Process 100 can implement one or more information retrieval processes. An example process of information retrieval can include the step of identifying a corpus of terms. Identifying a corpus can include, inter alia, collecting or identifying a set of textual materials, on the Web or held in a file system, database, and/or content corpus manager, for analysis. In one embodiment, the analytics system can apply advanced statistical methods. In another example, various natural language processing, such as part of speech tagging, syntactic parsing, and other types of linguistic analysis, can be implemented. A named-entity recognition process can use of various gazetteers and/or statistical techniques to identify named text features, inter alia: people, organizations, place names, stock ticker symbols, certain abbreviations, and so on. Disambiguation steps (e.g. using various contextual clues) can be applied. Recognition of pattern identified entities algorithms can be applied to identify various features (e.g. using regular expression or other pattern matches). Coreference steps can be implemented to identify noun phrases and other terms that refer to the same object. Relationship steps can be implemented for event extraction. Process can identify associations among entities and other information in text. Sentiment analysis can be applied as well. Text analytics techniques can be applied to analyze sentiment at the entity, concept, or topic level and/or in distinguishing opinion holder and opinion object. Quantitative text analysis can also be implemented.

Process 100 can also include a categorization process classifies the content into various medical conditions/health topics and subcategories within them. Categorization is the process in which ideas and objects are recognized, differentiated, and understood. Various categorization methods can be utilized, including, inter alia: classical categorization, conceptual clustering, prototype categorization, fuzzy clustering, various machine learning classification methods, etc. A corpus of tokens/terms can be manual created for various health-related categories (e.g. heart health, physical fitness tips, diabetes issues, cancer, women's health, etc.). These various corpuses can be used in a categorization/classification process.

Figure 2:
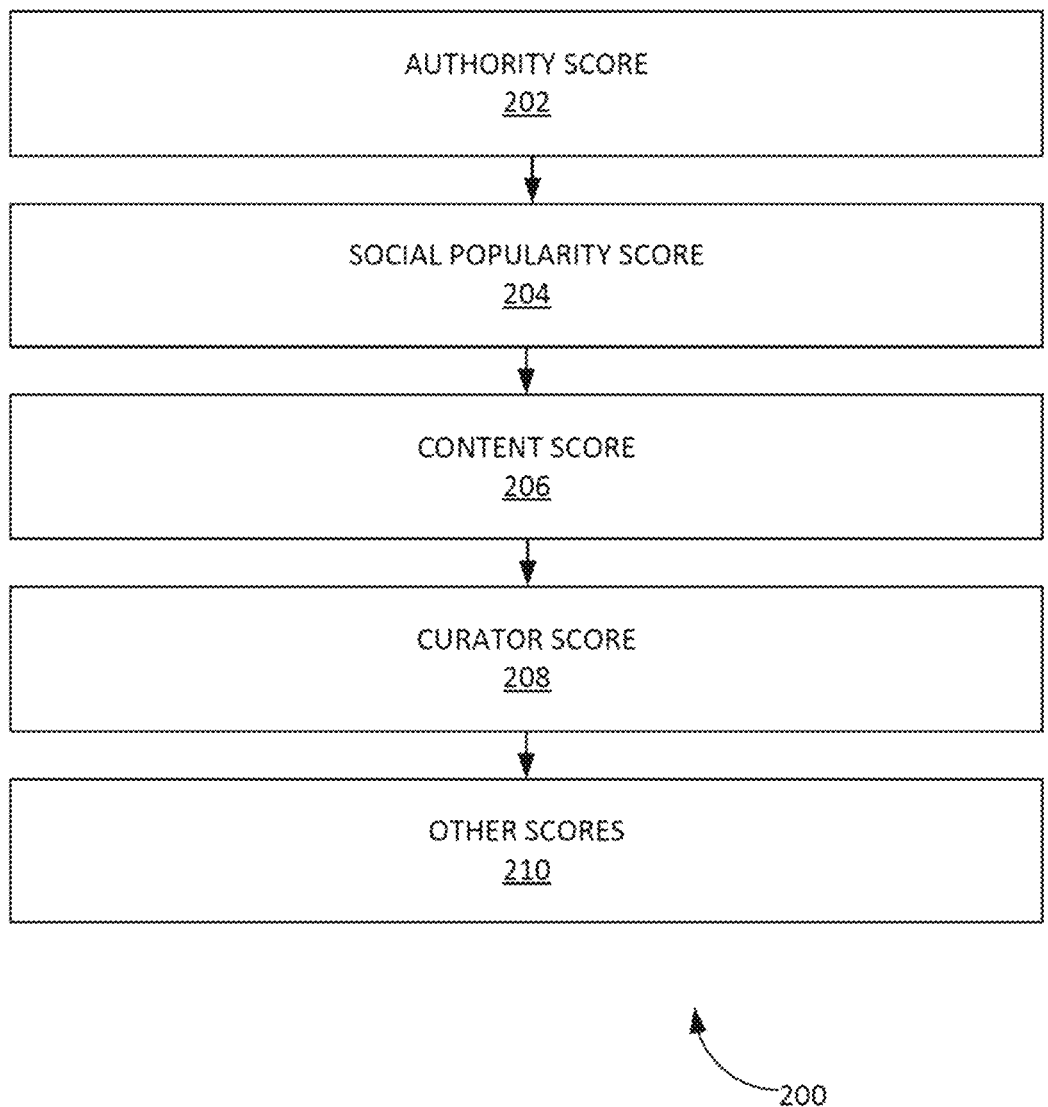
FIG. 2 illustrates an example process of scoring and ranking health content, according to some embodiments.

FIG. 2 illustrates an example process 200 of scoring and ranking health content (e.g. as provided step 106 of process 100), according to some embodiments. Process 200 can score a health content based on a variety of parameters/factors such as those provided in the various steps of process 200. Process 200 can include various functionalities for obtaining the information utilized to score health content (e.g. web crawlers, text analytics functionalities, calculators, statistics software, etc.). It can be determined that a health-content article actually includes health education content and not marketing content (e.g. in process 300 infra). Process 200 can then score accumulated article based on various parameters. For example, process 200 can determine an authority score in step 202. The authority score can be based various indicators that state the health content has been reviewed and approved by a medical expert (e.g. a medical doctor, a nurse, a medical researcher, etc.). In one example, process 200 can crawl into the content of an article (e.g. via a hyperlink). Process 200 can examine the article for a token that indicates that the article has been reviewed by a medical expert (e.g. the document file of a WebMD online article can have tokens that states "reviewed by so and so MD" etc.). Medically reviewed articles can weighted more than non-medically reviewed articles. Process 200 can maintain a list of tokens that indicate that articles are reviewed by medical experts. Another example an indicator that can be used to determine an authority score can be whether the article originated with a renowned/trusted/authoritative source (e.g. a hospital, a government health agency, a renowned health association like the American Diabetes Association, and the like). Accordingly, process 200 can maintain a list of highly rated hospitals and/or other highly rated health agencies/entities. When an article originates with a renowned health agencies/entities, it can receive a specified weighting added to its authority score. In one example, a list of twitter handles of hospitals can be maintained and followed on automated basis. This can be used to determine that health content has originated from the hospital.

Process 200 can determine a social popularity score in step 204. In one example, process 200 can track known medical experts (e.g. medical doctors, etc.) in social media. Process 200 can track the popularity medical experts' posts to health-content articles. Popularity can be measured by various factors, such as, inter alia: retweets, favourites, reposts, likes, number of comments, favourable comments, etc. In one example, process 200 can include sentiment analysis systems that review comments can determine a level of positive feed for the article in the comments. These parameters can be used to generate a social popularity score.

Process 200 can determine a content score in step 206. Process 200 can include text analysis and various matching algorithms to determine if specified tokens that indicate quality health content are in the article. For example, a content vocabulary (e.g. 'may be harmful to you', 'increases likelihood of', etc. and/or other text patterns) can be generated. If these patterns extant in the article then process can give the article a specified weight with the content score.

Process 200 can determine a manual score in step 208. An entity implementing process 200 can utilized a medical expert to curate health content. The medical expert can review health content and provide a manual score based on the medical expert's assessment as to the quality of the article's content and/or lack of marketing content. These scores are provided by way of example and not of limitation. Other scores can be used to ensure quality health content and/or deprecate lower quality health content and/or marketing content. Accordingly, process 200 can provide other scores in step 210. Scores 202-210 can be aggregated and used to provide an overall score for each health-content article. Health content can be ranked according to the various respective aggregated scores. It is noted that in one example, the various vocabularies of tokens/text used by process 200 can be manually generated by medical experts.

In another example, the tokens/text can be generated, in part, based on statistical analysis, backtesting algorithms, and/or machine-learning algorithms.

Figure 3:
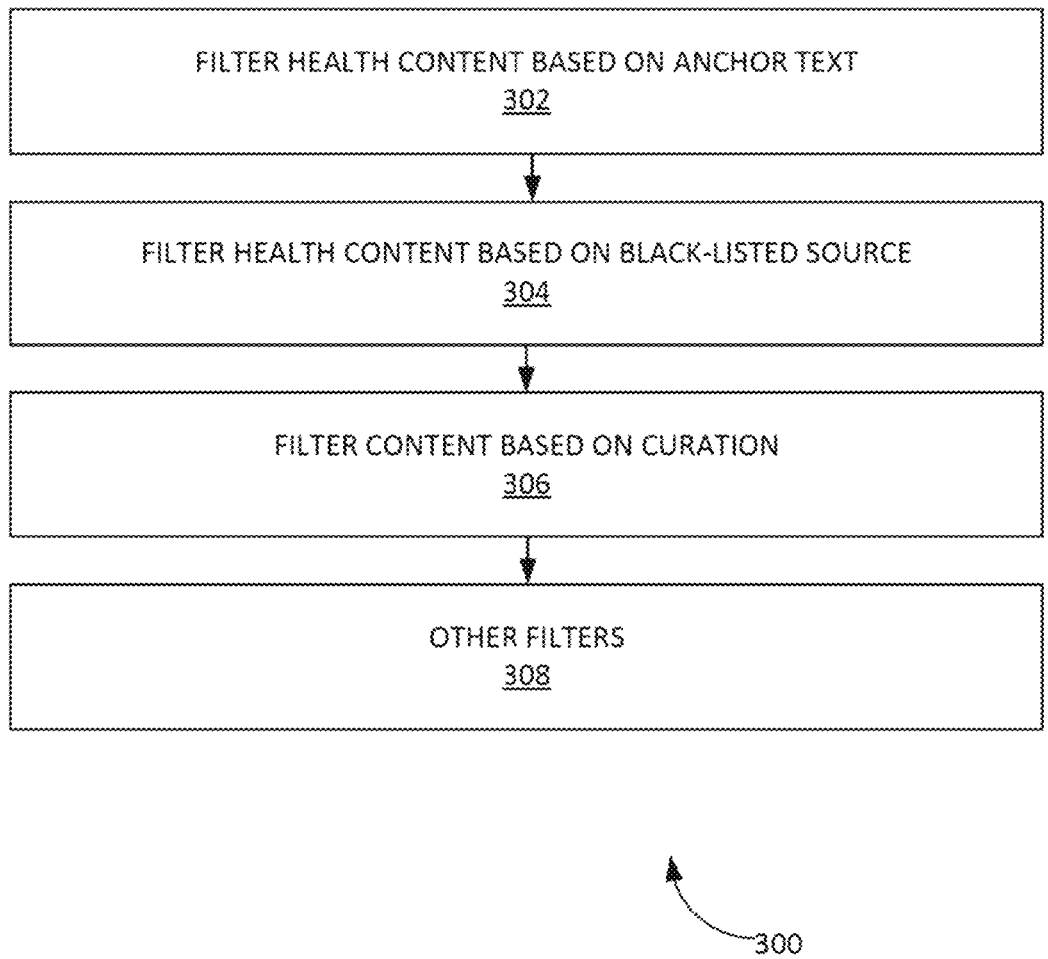
FIG. 3 illustrates an example process of filtering health-content articles (e.g. to remove articles that mostly marketing content, etc.), according to some embodiments.

FIG. 3 illustrates an example process 300 of filtering health-content articles (e.g. to remove articles that mostly marketing content, etc.), according to some embodiments. In step 302, process 300 can filter health content based on the content of the anchor text of the social network post that links to the health-content article. For example, process 300 can analyse a tweet. The tweet can be the anchor text and include a hyperlink to the article. Process 300 can search the anchor text for key words and pattern matches. Process 300 can include a developed vocabulary of tokens that can be compared to anchor text to identify whether anchor text is related to health education content as opposed to marketing content or quackery content.

In step 304, process 300 can filter content from a list of blacklisted content origins. For example, a blacklisted set of websites (e.g. quackery.com, etc.) can be maintained. If the hyperlink links to a blacklisted website, the article can be blocked from inclusion in the ranked health content. In step 306, health content can be filtered based on curator decisions. It is noted that vocabulary of tokens that can be used to identify marketing content. This can be applied both to the anchor text and/or title of article. If a match is determined then process 300 can jettison article. It is noted that, in step 308, other filters can also be implemented.

Figure 4:
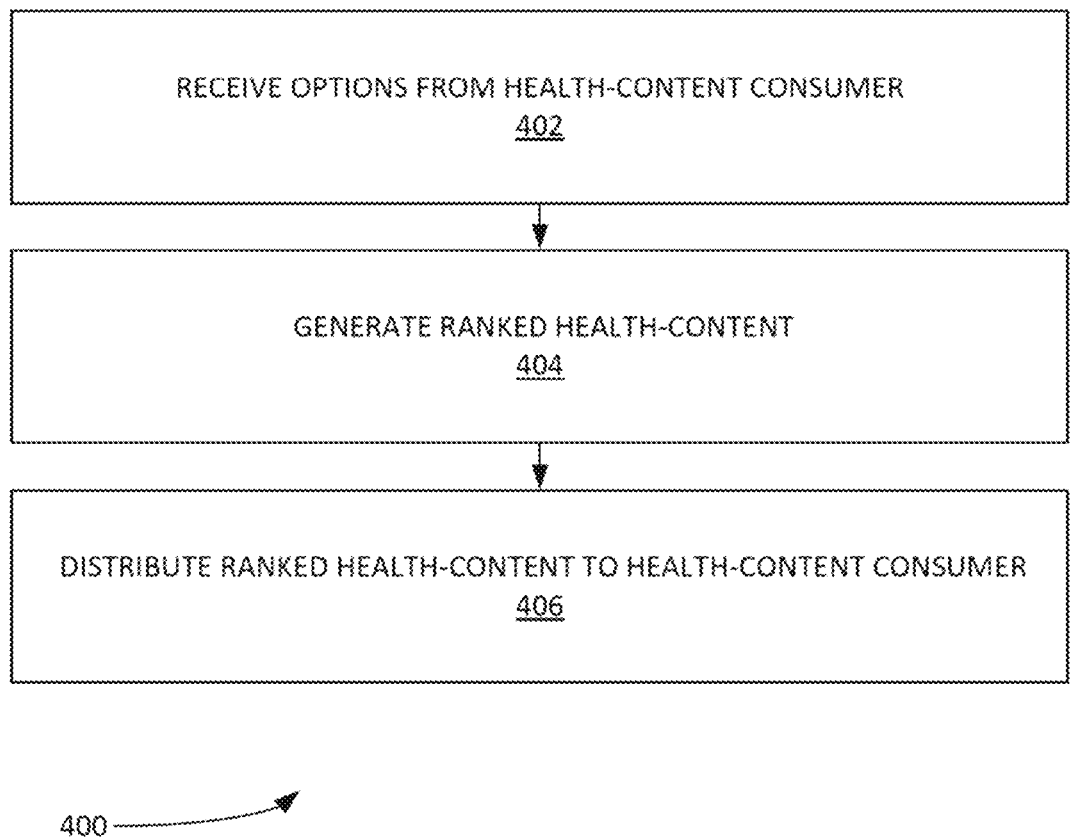
FIG. 4 illustrates an example process of published ranked health-related content, according to some embodiments.

FIG. 4 illustrates an example process 400 of published ranked health-related content, according to some embodiments. Process 400 can put ranked content into a periodically updated web feed and/or health-news feed. The feed can be provided to a hospital (and/or other health-care entity) as a consumer. The hospital can provided access to the feed via a private or public portal. Patients and/or other users can then view the feed content. The hospital can review incoming content and modify the content attributes (e.g. can chose social popular content and decrease medical authority content) and can also curate the health content. In some examples, the hospital can assign scores and/or manually adjust the parameters of processes 100-300. In this way, a specified version of a feed for a specific hospital.

In one example, in step 402, process 400 can receive manually selected options from a hospital (e.g. topics to include in feed, parameters to weight greater, update periods, etc.). In step 404, process can generate the ranked health-care content (e.g. using processes 100-300). In step 406, the ranked health-care content can be aggregated into a web feed/news feed format and pushed to the hospital's portal for publication (e.g. as a widget). A widget can be an applet intended to be used within web pages. It is noted that the output of process 100 and/or 400 can also be formatted to be pushed to a mobile device application and/or a wearable computing device display.

Example Systems and Architecture

Figure 5:
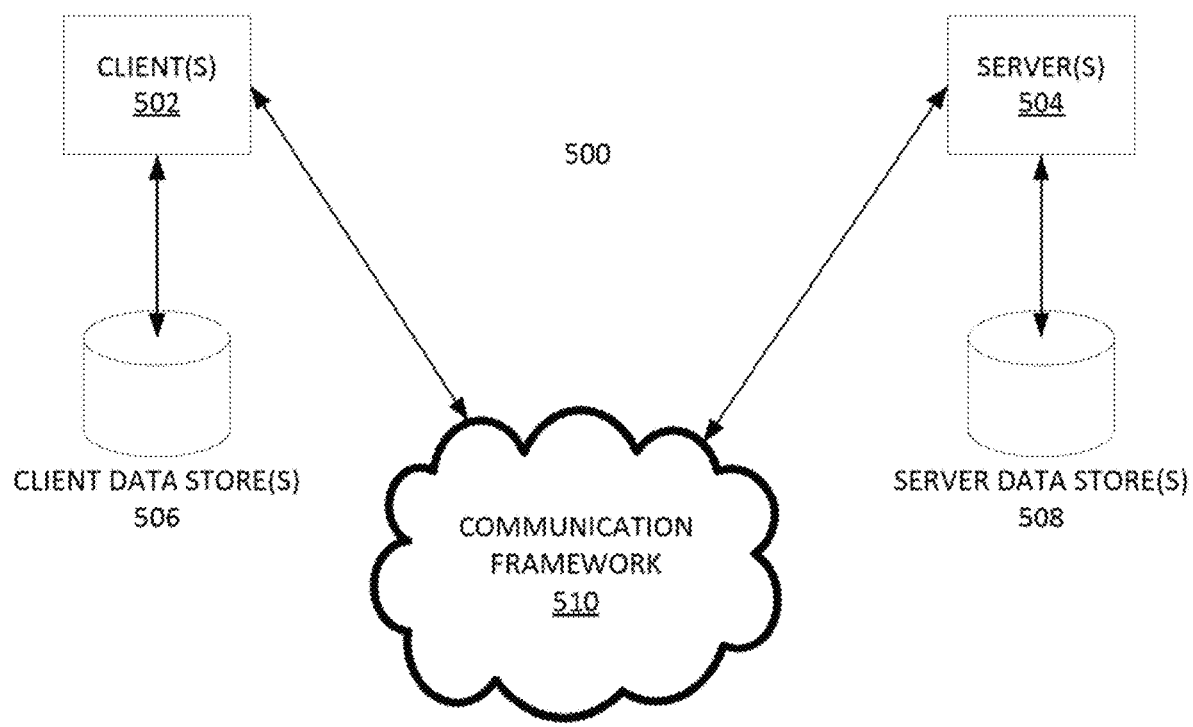
FIG. 5 is a block diagram of a sample computing environment that can be utilized to implement various embodiments.

FIG. 5 is a block diagram of a sample-computing environment 500 that can be utilized to implement various embodiments. The system 500 further illustrates a system that includes one or more client(s) 502. The client(s) 502 can be hardware and/or software (e.g. threads, processes, computing devices). The system 500 also includes one or more server(s) 504. The server(s) 504 can also be hardware and/or software (e.g. threads, processes, computing devices). One possible communication between a client 502 and a server 504 may be in the form of a data packet adapted to be transmitted between two or more computer processes. The system 500 includes a communication framework 510 that can be employed to facilitate communications between the client(s) 502 and the server(s) 504. The client(s) 502 are connected to one or more client data store(s) 506 that can be employed to store information local to the client(s) 502. Similarly, the server(s) 504 are connected to one or more server data store(s) 508 that can be employed to store information local to the server(s) 504.

Figure 6:
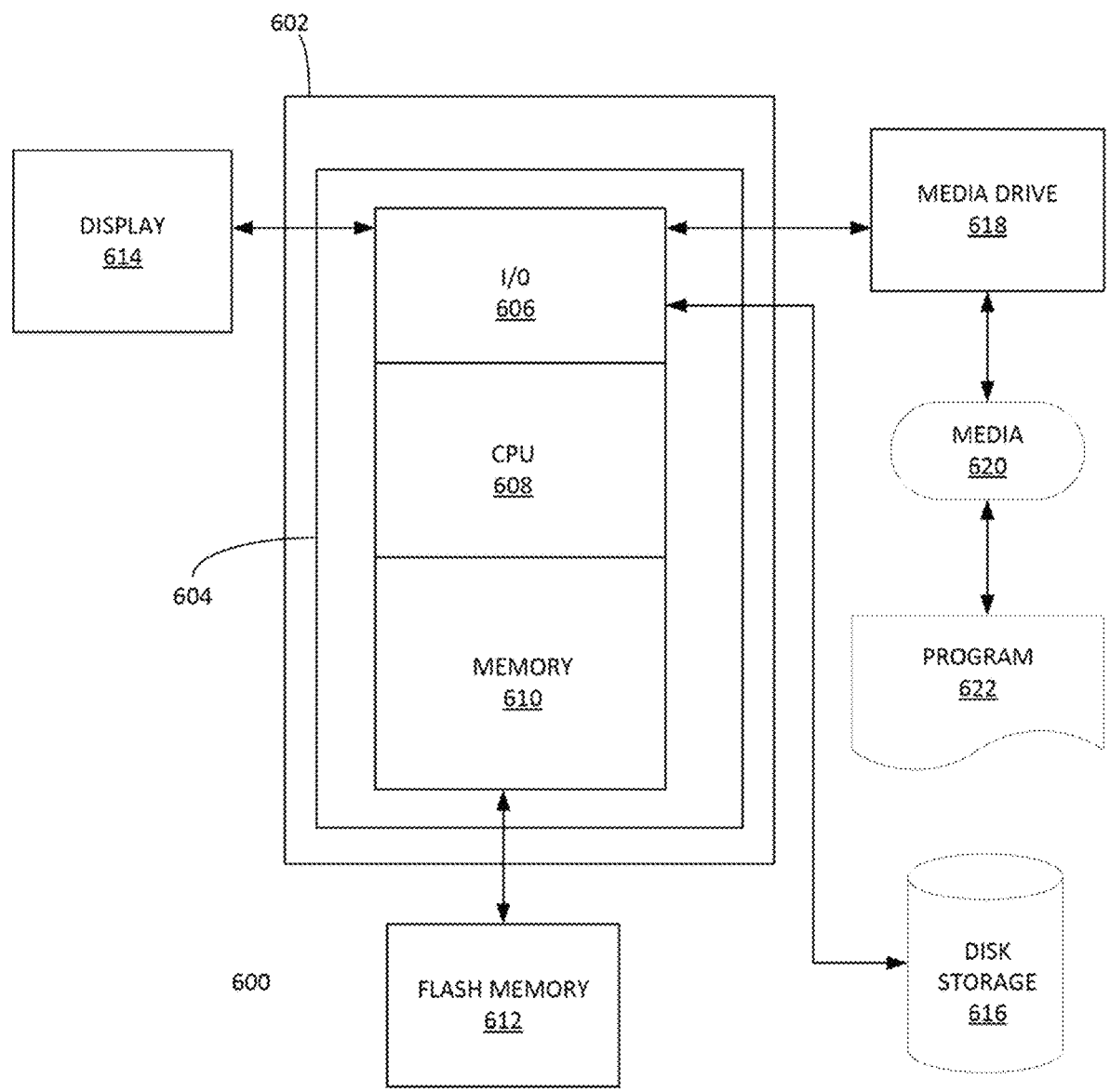
FIG. 6 depicts computing system with a number of components that may be used to perform any of the processes described herein.

FIG. 6 depicts an exemplary computing system 600 that can be configured to perform any one of the processes provided herein. In this context, computing system 600 may include, for example, a processor, memory, storage, and I/O devices (e.g. monitor, keyboard, disk drive, Internet connection, etc.). However, computing system 600 may include circuitry or other specialized hardware for carrying out some or all aspects of the processes. In some operational settings, computing system 600 may be configured as a system that includes one or more units, each of which is configured to carry out some aspects of the processes either in software, hardware, or some combination thereof.

FIG. 6 depicts computing system 600 with a number of components that may be used to perform any of the processes described herein. The main system 602 includes a motherboard 604 having an I/O section 606, one or more central processing units (CPU) 608, and a memory section 610, which may have a flash memory card 612 related to it. The I/O section 606 can be connected to a display 614, a keyboard and/or other user input (not shown), a disk storage unit 616, and a media drive unit 618. The media drive unit 618 can read/write a computer-readable medium 620, which can contain programs 622 and/or data. Computing system 600 can include a web browser. Moreover, it is noted that computing system 600 can be configured to include additional systems in order to fulfill various functionalities. Computing system 600 can communicate with other computing devices based on various computer communication protocols such a Wi-Fi, Bluetooth® (and/or other standards for exchanging data over short distances includes those using short-wavelength radio transmissions), USB, Ethernet, cellular, an ultrasonic local area communication protocol, etc.

Figure 7:
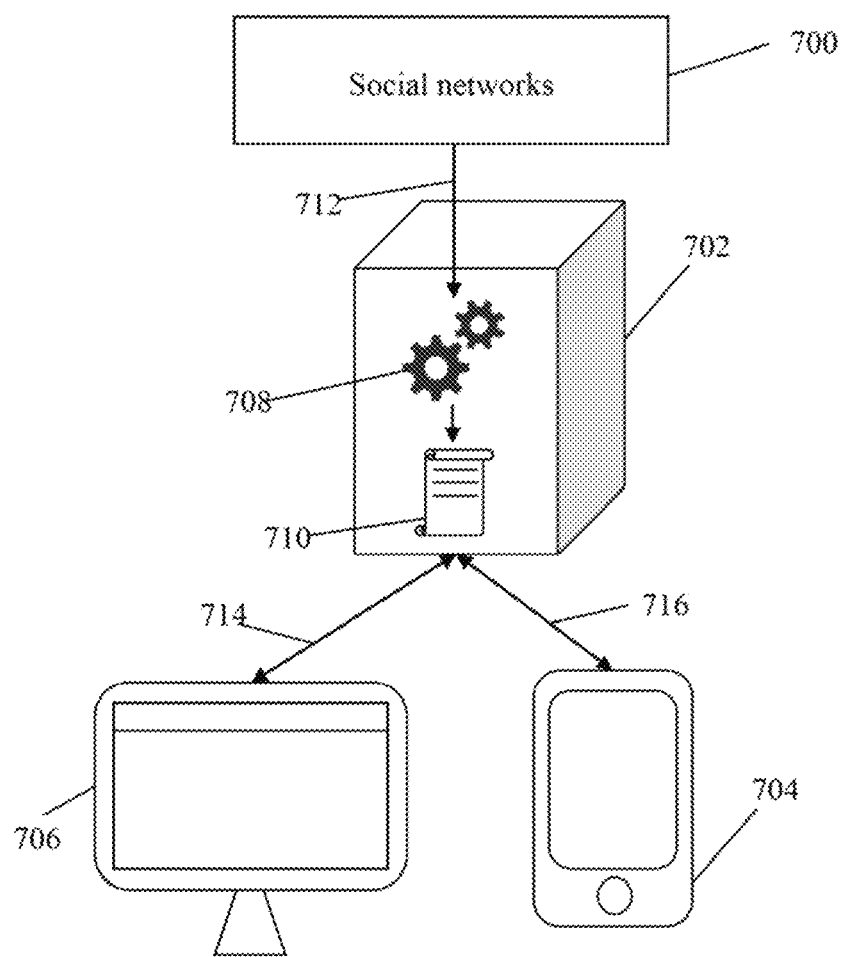
FIG. 7 provides an example system level view of the overall architecture utilized to implement various embodiments.

FIG. 7 provides an example system level view of the overall architecture utilized to implement various embodiments. 700 represents the set of social networks from which content is sourced, according to some embodiments. In broad terms, here the entity "social networks" represents any content source, where users post content and other users have the ability to express their opinions on the social post 710 represents the backend server of the content ranking engine that ranks online patient education content, sources content feeds for various medical conditions and health topics and responds to requests across a computer network from third-party products, 704 and 706. While, 704, represents a mobile device interface of a health portal, 706, represents a computer browser based interface of a health portal that sources content feeds from the content ranking engine. The presentation of content feeds for medical conditions and health topics will be different across the front ends as the user interface display is tailored to the form factor of the device in question.

Still referring to FIG. 7, 702, represents the backend server that hosts the content engine software, 708. Besides hosting the content engine, the server, 702, is also responsible for other functions such as, providing web service APIs that enable clients to source content feeds from the content engine, manage the overall working of the system, etc. The output of the content engine is a ranked ordered list of content specific to a medical condition. This ranked content is also grouped under subcategories for each medical condition. This is depicted as 710. The ranked list of content, 710, is served to patients on health portals accessed from front-end interfaces such as 704 and 706.

The server, 702, interfaces with the social network using a software API interface, 712, which fetches the content that matches the filter criteria. This interface, 712, is unique to each social network that the server uses as a content source, and the filter criteria used is unique to each social network as well. 714 and 716 are bidirectional interfaces that are used by the web health portal, 706 and the mobile device health portal, 704, respectively. These interfaces are used to source content to the health portals from the ranked list stored in the server for each specific medical condition. Content, that is promotional in nature, can also be sent to the health portal using these interfaces. Also, these interfaces are used to report back user engagement activity for each piece of content. Besides these functions specific to the content engine's functionality, these interfaces can also enable the health portal to request services and data from the server.

Figure 8:
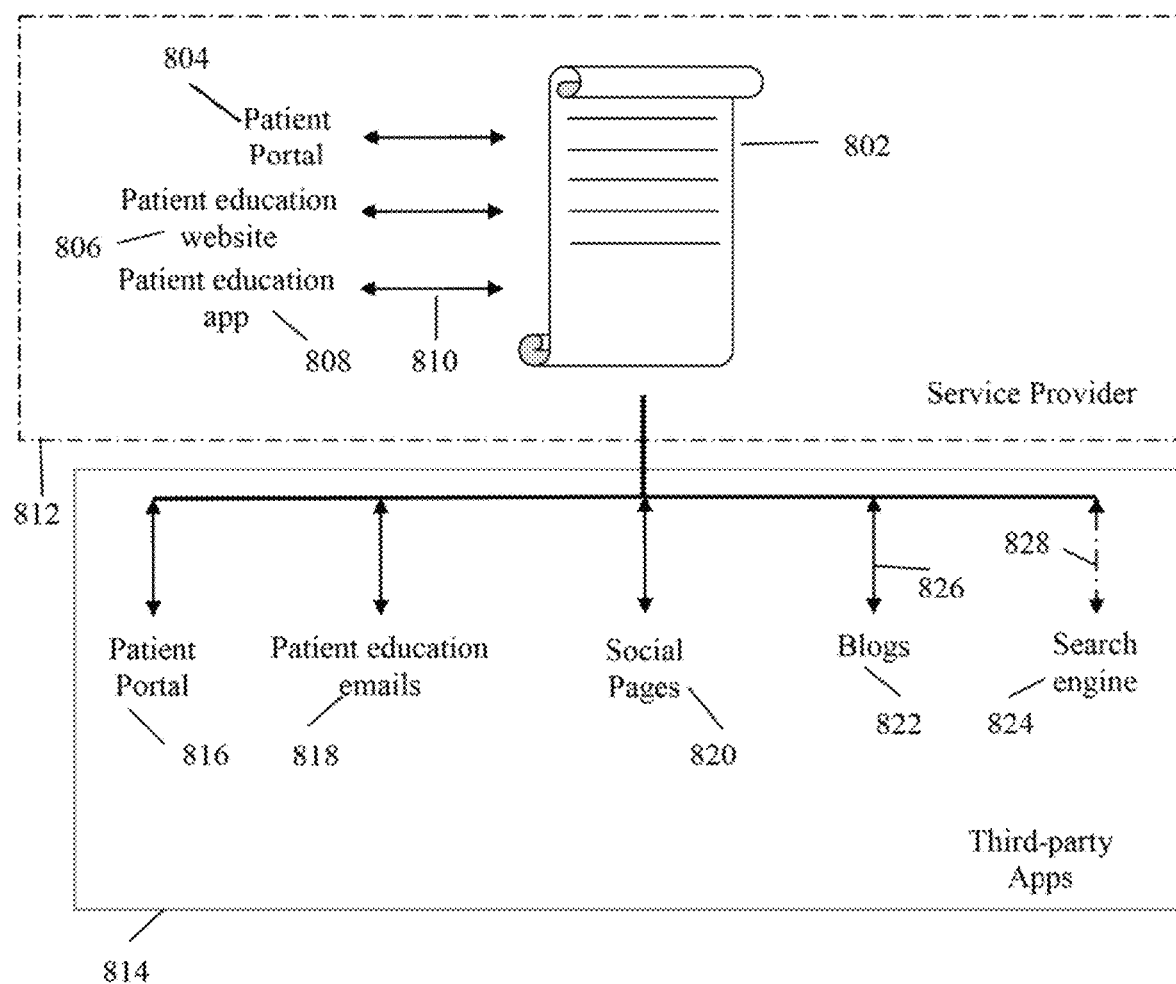
FIG. 8 depicts a set of service provider and third-party applications that source the ranked and subcategorized content for its users, according to some embodiments.

FIG. 8 depicts a set of service provider and third-party applications that source the ranked and subcategorized content for its users, according to some embodiments. 802 represents the ranked and subcategorized content for various medical conditions. 812 depicts the service provider's domain that includes the ranked content, 802 and a set of applications, 804, the patient portal application and/or website, 806, the patient education website and 808, the patient education app, all of which are launched and maintained by the service provider. The applications, 804, 806 and 808, source content from the ranked content list, 802, using a bidirectional API, 810. The API, 810, also enables the applications to send user engagement statistics and other analytics information back to the content engine, 802.

The set of all third-party applications that source content from the content engine is depicted by 814. This includes a patient portal app, 816, a patient education email service, 818, a social page for health-related activities, 820, a blog relating to health care, 822, and a conventional search engine, 824. The applications, 816, 818, 820 and 822, use the API interface, 826, which enables these applications to make a request for content with certain parameters and receive a response with content corresponding to the request. The ranked content is shared with the applications in incremental parts as requested. The search engine app, 824, is an example of an application that uses the ranked content, 802, as a whole. The entire copy of the ranked content is shared with the search engine application and the continuously updated content's rankings are shared with the third-party application. This functionality is encapsulated by the API, 828.

Example Use Case

The example use case includes a method and apparatus for sourcing ranked online patient education content wherein a content ranking engine aggregates, scores and ranks online patient education content that obtains published every day, categorizes the content into various medical conditions and health topics and exposes software Application Programming Interface (APIs) for users and third-party companies to source ranked content feeds. These content feeds are different from regular RSS feeds as the content is generated from all online websites as opposed to specific ones chosen by the user and the feeds are ranked based on their quality. The content ranking engine uses a multistage sophisticated ranking algorithm that uses information gleaned from social media to score an article based on its authority, popularity, content quality, etc. and thereby create a ranked list of content for various medical conditions and health topics.

The ranked and subcategorized list of content for various medical conditions, herein referred to as "ranked content", can be sourced to health portals, patient portals, direct to consumer mobile applications, direct to consumer websites, wellness portals, health websites, etc. and serve both as a source of information and as a tool to increase user engagement of the portal.

One embodiment can include a content ranking engine, herein referred to as the "content engine", which uses information gleaned from social media to seek and curate educational content published on the Internet for various medical conditions and health topics. The content engine is hosted, maintained and managed by a service provider, herein also referred to as "provider", who will make the service available to both service provider products and third-party products, including but not limited to, patient portals, health-related websites, health-related mobile applications, social networking pages, blogs, electronic medical record software, patient education emails, etc., as a whole, in parts or as a service exposed in the form of application programmable interfaces (APIs).

The content engine comprises of input content, including but not limited to web content such as links, educational pictures, articles etc. gathered by a web crawler, social media content such as posts, tweets, pins, etc. that contain web links with patient education articles, educational pictures, etc. gathered from social media, etc., a filtering process wherein the automatic process parses each piece of input content collected and determines if the content is patient education material, a categorization process, wherein an automatic process parses each piece of input content collected and classifies the content under various categories of medical conditions and health topics, a ranking process that scores and ranks articles based on a number of parameters including but not limited to the authority of the article, social popularity of the article, the content quality of the article, etc., an attributes assignment process, wherein an automatic process parses each piece of content collected and assigns certain attributes based on certain characteristics found within the piece of content, a manual process wherein the service provider's operator verifies general sanity of the algorithm's results and makes necessary changes as appropriate and an output that is a ranked list of content specific to a medical condition/health topic.

The content engine can be configured to run for any one or many possible triggers including but not limited to a time trigger, wherein the content engine runs at one or multiple specified times every day, a vocabulary change trigger, wherein the content quality measurement vocabulary currently used by the algorithm has changed, the social score for a piece of content has changed in response to new social activity for the content in social networks, the manual curation process removed a few pieces of content, a social content source trigger, wherein the set of social network sources has changed, the set of content sources within a specific social network has changed, etc. For every run of the content engine, the ranked content is updated with the results.

The content engine relies on the fundamental premise that in an increasingly social world, people quite readily share content with their social networks that they find useful, informative and interesting. The implication of this common trend is that if a particular piece of content is indeed useful, informational and interesting, it will find its way into social media. In other words, patient education content collected from various social networks serves as a worthwhile proxy to useful, informational and interesting patient education content published online. To limit the scope of content to a specific subject and to a reasonably acceptable processing limit, the content engine is manually and/or automatically seeded with a set of filters, including but not limited to, keywords, tags, identifiers, groups, pages, etc. specific to a medical condition. This set of filters will be different from one social network to another and from one medical condition to another. For example, for diabetes as the medical condition and Twitter as the social network, the filter set is a group of hashtags, such as #diabetes, #dlife, #type1, #type2, #hbalc, etc. As part of the first stage of the process, the content engine gathers content that matches the filter criteria. An alternate conduit for sourcing online patient education content would be an automated web crawler process that sources, content into the content engine using one of several ways, including but not limited to, scouring the entire Internet for content and the collected content is then parsed by a second process that separates out health and medical content from the rest, sourcing content from a predefined list of health and medical websites, sourcing content using software interfaces exposed by popular search engines etc.

The second stage of the content engine process uses a sophisticated filtering algorithm that parses each piece of input content collected and determines if the content is patient education material so that it could be used for further consideration by the content engine. During this process, the algorithm rejects advertising, promotional and other content that even though has a relevance to a specific medical condition, is not educational, informative or instructive. The algorithm uses multiple factors to filter content, including but not limited to, parsing the social media message, herein referred to as the "anchor text" of the social media post, that serve as the prelude to the web link for matching word patterns from a predefined vocabulary of health and medical related terms, herein referred to as the "filter vocabulary", web crawling the link to extract the title of the web article to check for filter vocabulary matches, web crawling the actual contents of the article to check for filter vocabulary matches, using social media identities of people who have interacted with the social media post to check for healthcare and/or medical experts, looking for categories of social media content that have been tagged with a specific identifier etc. Content selected by the filtering algorithm is used for further consideration by the content engine while the rest of the content is discarded.

The third stage of the content engine process, the categorization process, begins the dual task of categorizing the piece of content into various medical conditions/health topics and subcategorizing the piece of content into various topics within a specific medical condition/health topic. Content is classified into various medical conditions/health topics through a number of techniques, including but not limited to, the social media keyword, tag, identifier, group, page, etc. associated with the content, a match of the anchor text, content item title, content text, etc. against a preset vocabulary of word patterns, one set of patterns for each medical condition/health topic, herein referred to as the "categorization" vocabulary, etc. Each piece of content within a medical condition/health topic is further subcategorized into various topics. For example, content within the health topic "Smoking" is further categorized into subcategories such as "General", "Harmful Effects of Smoking", "Benefits of Quitting.", "Quitting tips". "eCigarettes", etc. The automatic process of sub categorization uses the same techniques as the categorization process. The categorization vocabulary is replaced by a vocabulary of word patterns, one set of patterns each for each subcategory within a medical condition/health topic, herein referred to as the "sub categorization" vocabulary.

The fourth stage of the content engine uses a sophisticated algorithm to score and rank each piece of content that has made its way this far along the content engine's processes and filters. The ranking process uses multiple factors to score content, including but not limited to, measuring the authority of the source of the article, herein referred to as the "authority" score, determining the social popularity of the article in various social networks, herein referred to as the "social" score, evaluating the content quality of the article, herein referred to as the "content" score, assigning an individual score for each piece of content by a manual process, herein referred to as the manual score, determining the levels of patient engagement for a piece of content, herein referred to as the patient score, etc. The final step of the scoring and ranking process involves creation of the ranked content for each subcategories of a specific medical condition by using a unique algorithm that combines one, few or all of the authority, social, content, manual and patient scores for each piece of content in a weighted manner.

The calculation of the social score depends on the premise that content obtains liked, commented and shared further within the social network based on its quality, whereby the social popularity and virality of a piece of content is a rough indicator of the quality of the content. The scoring and ranking process of the content engine uses a sophisticated algorithm to calculate a social score for each piece of content. The algorithm uses multiple factors to calculate the score, including but not limited to, the number of social actions on the content such as shares, likes, favorites, comments, etc., the nature of comments received, a hierarchy of importance of various social actions taken by users on the content, trending patterns for the same piece of content on other social networks, social actions taken by a specific entity or individual on the content, the relative importance of a specific source of the content, the geographic location of the source of the content etc. The social score of a piece of content will vary by time and will be recalculated every time the content engine runs.

When people take actions on a post that they see in social media by either sharing, liking, commenting or retweeting, the identity of the action taker is now associated with the social media post. The calculation of the authority score depends on the premise that if a very reliable source of information takes actions on a social media post, then that is a rough indicator of the quality of the article and thereby the authority score. The algorithm uses multiple factors to calculate the authority score, including but not limited to, assigning a predetermined score based on the category of the entity, fetching the social influence score of an entity from a third-party company, determining the score based on the type of social action taken by a certain entity, etc. The authority score for a piece of content is updated for every new activity that happens on the social media post that contains the article.

The calculation of the content score is based on the premise that a well written patient education article has certain characteristics and by looking for those characteristics, the quality of the article can be determined and thereby the content score. A well written health education article has a certain signature, including but not limited to, being informational, instructive, and advisory, etc. in nature. A vocabulary of word patterns, herein referred to as the "content" vocabulary, helps in determining the amount of informational, instructive and advisory content within the article. Each piece of content is scored for matching word patterns in the content vocabulary to determine the content score of the article.

The content engine calculates a patient engagement score for each piece of content by measuring the level of patient engagement that a piece of content receives. The patient's engagement with a piece of content is measured in a number of ways, including but not limited to, the click through rate of the content, the percentage of the content that the user read, the number of comments, likes, shares, etc. received, the nature of comments received, the amount of time spent on a piece of content, the type of content etc. This score is updated on a continuous basis to reflect for new patient engagement activity on the content. A new piece of content that has just been sourced into the content engine and assigned social and manual scores will not have a patient score as it has not been shown to patients yet. A starting patient engagement score will be assigned based on any one of the following techniques, including but not limited to, an average of the social and manual scores assigned to the content, half of the maximum patient score possible, same as the manual score, etc.

The fifth stage of the content engine is the attributes assignment stage, wherein each piece of content is parsed and any applicable attributes are assigned to it. The attributes help in identifying content with certain characteristics which can then be used by customers for sourcing content that has certain attributes. The attributes supported can include, without being limited to, a "medically reviewed" attribute, wherein the article has been reviewed by a medical professional, a "provider's content" attribute, wherein the content was written and/or endorsed by a large hospital, a "health agency content" attribute, wherein the content was written and/or endorsed by a federal or state government health agency or an organization such as American Diabetes Association, American Cancer Association, etc., a "physician's content" attribute, wherein the article was endorsed by a physician on social media, etc. The assignment of attributes is done algorithmically using a number of techniques, including but not limited to, using the social identity of the user endorsing a piece of content, parsing the content of the article to look for pattern matches that indicate the content was medically reviewed, using the content's certification status provided by agencies such as Health On the Net Foundation, etc.

The sixth stage of the content engine process is a manual stage wherein the service provider's manual operator assigns a manual score for each piece of content based on the quality and relevance of the content. The manual stage also verifies the general sanity of the algorithm and takes actions, including but not limited to, rejecting pieces of content that are promotional in nature but have been missed by the filtering process, remarking categorization of pieces of content that have been miscategorized by the automatic process, remarking sub categorization of pieces of content that have not been correctly subcategorized by the algorithm, marking articles with the correct attributes that have been previously mismarked etc.

The content engine can be configured to run in different modes, including but not limited to, certain stages of the content engine are skipped, changed or replaced by an equivalent stage, sequencing of the various stages of the content is changed, algorithmic steps of an individual stage are skipped, changed or replaced by an equivalent step, smaller subset of the overall scores used in the ranking process, etc. Such changes can be done to optimize the resulting output for various scenarios, including but not limited to, a customer specific stream, a medical condition/health topic specific stream, a subcategory specific stream, an attribute specific stream, etc.

The output of the content engine is the ranked and subcategorized content feeds for various medical conditions and health topics. Customers can choose to have an additional optional stage wherein customers can influence the content selection and ranking process for their patients. This creates a ranked list of content specific to the customer and the customer's patients. The customer's operator can do any one of several things, including but not limited to, change the ranking of content by adjusting the previously assigned manual score for the content, discard certain pieces of content for further stages of the content selection process, change the current categorization of the content, add new pieces of content, etc. This gives additional capabilities for the customer to customize the delivery of patient education material for its users that match with other aspects of its healthcare delivery mechanisms.

A different version of the output is created for customers that opt to receive a customized version of the output. For each new login session of the user into the customer's health portal, new content is sourced from the server based on the ranked list of content. Since the patient's engagement with each piece of content is tracked for the calculation of the patient score, content that the user has already seen is not shown to the user again. This ensures that the user sees fresh, new and changing content at every login into the health portal.

Besides serving educational content to users of a health portal using the ranked and subcategorized list of content, such content can also be sourced to other products owned and maintained by the service provider or a third-party, either as a whole or in parts. This is done by exposing Application Programmable Interfaces, herein referred to as "APIs" or "developer APIs", that enable the content engine to source the ranked content. An invocation of the API with parameters including but not limited to, the desired medical condition, the subcategories within the medical condition desired, the number of results requested, etc. results in the content engine being queried and the set of results returned back to the API caller. The APIs also enable the product to send back levels of user engagement and other applicable pieces of analytics information on each piece of content back to the content engine for further refinement of the rankings.

The ranked content served in response to an API invocation can include content that is promotional in nature such that a "free" version of the developer APIs can be monetized by the service provider. The results returned by a "paid" version of the developer APIs will only contain the requested content. The ranked content can also be shared in whole with a service provider's product or a third-party's product. A different set of APIs enable the sharing of the content in whole, including but not limited to, initial sharing of the entire content, sharing of content for a specific medical condition, subsequent updates to the content after the initial transfer of data, etc.

The service provider can provide an alternate implementation to the APIs by providing a Software Development Kit, herein referred to as "SDK", which can be used by third parties to source the service provider's ranked content. The SDK comprises of a number of software elements packaged together, including but not limited to, a structured and formatted front-end interface that displays content received from the service provider, a set of bidirectional APIs that interface with the service provider's content engine, supporting files that enable the SDK to be seamlessly included with the third-party's browser or mobile front-end software code, etc. The SDK provides an extremely quick and easy way for third parties to include the service provider's content in their products.

The product described herein is based on the premise that in an increasingly social world, people share content with their social networks that they find useful, informative and interesting. This user behavior is tapped to seek and curate relevant educational content for a specific medical condition. The content engine processes the content through multiple automatic and manual stages, scores, the content based on its quality and information and uses sophisticated algorithms to create a ranked order list of content grouped under appropriate subcategories for a specific medical condition. These content feeds can now be used as a tool to personalize the contents of a health portal and thereby increase the user engagement of the health portal.

An example of calculating a social popularity score is now provided. A social popularity score can be a number from one to one hundred (1-100). A web article may have received twenty-two (22) likes, three (3) shares in Facebook®, eighteen (18) favorites, twenty-one (21) retweets on twitter, twenty-six (26) likes on LinkedIn, etc. These various social popularity numbers from various social networks can be converted into one scaled number from one to one-hundred (1-100). For example, one-hundred (100) can be divided into equal parts based on the number of social networks that are being considered (e.g. three (3)). For example, considering a measure of Facebook® likes, a sample set of about one-thousand (1000) health-education articles (e.g. from which marketing articles have been filtered out) and the number of likes for each article can be obtained and a mean can be calculated. A cumulative-probability distribution curve can be used to translate the "likes" number of an incoming article modeled on a curve whose mean was calculated in the first step.

A social post is most active in its earliest phase and rapidly declines in popularity as time goes on. In other words, the popularity lifetime of a social post can be modeled as a downward sloping exponential curve. This can be modeled as an exponential distribution (because of the nature of social posts activity). Using the above, the "likes" of an article can be translated to an absolute number. The step can be individually repeated for each social popularity component of each social network considered.

The systems and methods provided herein can be applied to other fields/verticals. For example, the systems and methods provided herein can be used to find top content feeds in the security area and distributed to portals used by information technology (IT) security professionals to monitor the security of the network. The systems and methods provided herein can be applied to provide a cloud-based network monitoring, security, risk, and/or compliance software that enables healthcare entities, retailers and/or other entities that handle sensitive health, credit card and/or personal information to meet security guidelines. Security professionals at these companies use an administration-web portal to obtain status updates on their various security, risk and compliance metrics.

The administration-web portal can provide a content widget that provides targeted content feeds specific to the profile type of the security professional. For example, a security professional at a hospital cares about HIPAA regulations, but does not care about PCI (credit card industry) regulations.

A health education article written by Mayo Clinic, two (2) years back, may still be valuable today. However, since, security regulations are often updated and/or modified (e.g. new computer viruses, etc.), an old article, even though written by a reputed security agency, may not be currently relevant. Accordingly, recency of information can be important.

Geographical relevance can also apply in a computer security implementation. The content engine looks at breach related articles (e.g. classifies it as a breach related article based on keyword matching results) and also tags them with a location. This can be done using Named Entity Recognition and automatically tags the article with a location based on the place entities found within the article. A curator can review these location assignments for correctness. These feeds can then be served appropriately to the end user base based on their location. Instead of a set of reputed hospitals and health agencies whose content and endorsement are valued higher, a list of reputed security field authors, publications, etc. can be utilized. Articles written by certified professionals (for example: CISSP certified) can be weighted higher. Popularity, and content scores work can work as the examples provided supra (e.g. with a security-related content vocabulary).

CONCLUSION

Although the present embodiments have been described with reference to specific example embodiments, various modifications and changes can be made to these embodiments without departing from the broader spirit and scope of the various embodiments. For example, the various devices, modules, etc. described herein can be enabled and operated using hardware circuitry, firmware, software or any combination of hardware, firmware, and software (e.g. embodied in a machine-readable medium).

In addition, it can be appreciated that the various operations, processes, and methods disclosed herein can be embodied in a machine-readable medium and/or a machine accessible medium compatible with a data processing system (e.g. a computer system), and can be performed in any order (e.g. including using means for achieving the various operations). Accordingly, the specification and drawings are to be regarded in an illustrative rather than a restrictive sense. In some embodiments, the machine-readable medium can be a non-transitory form of machine-readable medium.

What is claimed is:

1. A computerized method for implementing a ranked health-content article feed comprising:
    obtaining a set of health-content articles, wherein a health-content article comprises a distributable computer file containing a media content comprising text, a digital image or a digital video, wherein the step of obtaining the set of health-content articles further comprises,
        with an automated web crawler,
            receiving the distributable computer file containing a media content comprising text, a digital image or a digital video,
            determining, by a processor, that a social media post comprises an anchor text related to a health content and a hyperlink to the health-content article by searching the anchor text for a set of key words and pattern matches that match a developed vocabulary of tokens that to the anchor text to identify that anchor text is related to health education content as opposed to marketing content or quackery content, and obtaining a set of statistics about the post, wherein the set of statistics comprises a number of social media post views, a number social media post likes, or a number of social media post shares within a social media network;

identifying a sub-set of health content articles comprising a marketing content, wherein the step of identifying the sub-set of health content articles further comprises:

generating a corpus of tokens that indicate that the health-content article comprises the marketing content;

matching the health-content article text with a specified number of tokens;

removing the sub-set of health content articles comprising the marketing content from the set of health-content articles, wherein the step of removing the sub-set of health content articles comprises, providing a set of blacklisted websites;

determining that the hyperlink in the social media post links to a blacklist website; and removing the health-content article that originates from the blacklisted website;

providing an authority score for each health-content article of the set of health-content articles, wherein the authority score is based on an indicator in a web page source of the health-content article that indicates that health-content article has been approved by a medical expert;

providing a social-popularity score for each health-content article of the set of health-content articles, wherein the social-popularity score is based on the set of statistics about the post obtained by the automated web crawler;

providing a content score for each health-content article of the set of health-content articles;

aggregating the authority score, the social-popularity score and the content score for each health-content article;

ranking the set of health-content articles based on an aggregated score of each health-content article; and distributing a ranked set of health-content articles to a consumer entity in a web-feed format by communicating the ranked set of health-content articles to a consumer entity in the web-feed format to a hospital server for display as a widget on a web page on a hospital patient portal.

2. The method of claim 1, wherein the medical expert comprises a medical doctor.

3. The method of claim 2, wherein the social-popularity score is based on a number of times the health-content article has been reposted in one or more social media websites.

4. The method of claim 3, wherein the content score is based on a text analysis determination that the health-content article comprises a set of specified tokens that indicate that quality health content is included in the health-content article.

5. A computerized system for implementing a ranked health-content article feed comprising:

a processor configured to execute instructions;

a memory containing instructions when executed on the processor, causes the processor to perform operations that:

obtain a set of health-content articles, wherein a health-content article comprises a distributable computer file containing a media content comprising text, a digital image or a digital video, wherein the step of obtaining the set of health-content articles further comprises, with an automated web crawler, receive the distributable computer file containing a media content comprising text, a digital image or a digital video, determine, by a processor, that a social media post comprises an anchor text related to a health content and a hyperlink to the health-content article by searching the anchor text for a set of key words and pattern matches that match a developed vocabulary of tokens that to the anchor text to identify that anchor text is related to health education content as opposed to marketing content or quackery content, and obtain a set of statistics about the post, wherein the set of statistics comprises a number of social media post views, a number social media post likes, or a number of social media post shares within a social media network;

identify a sub-set of health content articles comprising a marketing content;

remove the sub-set of health content articles comprising the marketing content from the set of health-content articles;

generate an authority score for each health-content article of the set of health-content articles;

generate a social-popularity score for each health-content article of the set of health-content articles;

generate a content score for each health-content article of the set of health-content articles;

calculate the authority score, the social-popularity score score and the content score for each health-content article;

rank the set of health-content articles based on an aggregated score of each health-content article; and distribute a ranked set of health-content articles to a consumer entity in a web-feed format.

* * * * *